United States Patent [19]

Stockinger

[11] Patent Number: 5,063,157
[45] Date of Patent: Nov. 5, 1991

[54] SERUM-FREE CULTURE MEDIUM FOR MAMMALIAN CELLS

[75] Inventor: Hubertus Stockinger, Penzberg, Fed. Rep. of Germany

[73] Assignee: Boehringer Mannheim GmbH, Mannheim, Fed. Rep. of Germany

[21] Appl. No.: 295,813

[22] Filed: Jan. 11, 1989

[30] Foreign Application Priority Data

Jan. 18, 1988 [DE] Fed. Rep. of Germany ....... 3801236

[51] Int. Cl.$^5$ .................. C12N 5/00; C12N 5/02; C12Q 1/68
[52] U.S. Cl. ................ 435/240.2; 435/240.25; 435/240.3; 435/240.31; 435/6
[58] Field of Search ............ 435/240.31, 740.3, 240.4, 435/740.5, 740.45, 740.54, 241, 6

[56] References Cited

U.S. PATENT DOCUMENTS 4,816,401  3/1989  Taupier et al. ................ 435/240.31

FOREIGN PATENT DOCUMENTS 0066284  8/1982  European Pat. Off. .

OTHER PUBLICATIONS

Paul et al., (1987) Thrombosis Research vol. 46 pp. 793–801.
Aznar et al. (1967) Nature 213, pp. 1251–1252.
Kindess et al. (1979) Thrombosis re Kindness et al. (1979) Thrombosis Research vol. 16, pp. 97–105.
Article-Arch. Int. Pharmacodyn. 282, 196–208 (1986).
Thrombosis and Haemosstasis, 58, 154 (1987).

*Primary Examiner*—Elizabeth C. Weimar
*Assistant Examiner*—Gian Wang
*Attorney, Agent, or Firm*—Felfe & Lynch

[57] ABSTRACT

The present invention provides a serum-free culture medium for mammalian cells, especially non-adherent cells, containing a base medium, transferrin, insulin and selenite, wherein it contains or consists of
  2 to 10 mg./litre transferrin,
  2 to 10 mg./litre insulin,
  1 to 10 g./litre peptone,
  10 to 500 mg./litre beta-D-xylopyranose substituted with phosphate, carboxyl and/or sulphate groups,
  0.1 to 0.5 mg./litre selenite and
  0.1 to 2 mg./litre biological polyamine.

17 Claims, No Drawings

SERUM-FREE CULTURE MEDIUM FOR MAMMALIAN CELLS

The present invention is concerned with a serum-free culture medium for animal and human cells and especially for non-adherent cells.

The culturing of animal and human cells, especially for the production of cell products, such as proteins via recombinant DNA, is of ever increasing importance. When these cell culturings are carried out on an industrial scale, large amounts of culture media are required.

As culture media, there have hitherto been used the most varied media, for example DMEM medium (H. J. Morton, In Vitro, 6, 89/1970), F12 medium (R. G. Ham, Proc. Natl. Acad. Sci. USA, 53, 288/1965) and RPMI 1640 medium (J. W. Goding, J. Immunol. Methods, 39, 285/1980; JAMA 199, 519/1957). However, when cells (non-adherent, anchorage-dependent cells) are to be cultured in suspension, serum must be added to these media. As a rule, for this purpose foetal calf serum, horse serum or human serum is used in a concentration of from 1 to 15% and usually of 5%. However, these sera are expensive and can scarcely be obtained in large amounts. A reduction of the concentration in the medium could hitherto not be achieved since the cells then aggregate to an ever greater extent, the cell aggregation then being most strongly marked when the cells are subject to serum-free culturing. Such aggregated cells die off very quickly so that the yield of the desired cell product decreases drastically.

For this reason, there is a great interest for serum-free media in which non-adherent cells can be cultured without aggregation. Thus, for example, in In Vitro Cell. Dev. Biol., 21, 588–592/1985, there is described a serum-free medium which is said to be suitable for culturing CGO cells and contains a 1:1 mixture of Ham's F12 medium and DMEM to which transferrin, insulin and selenite have been added. Apart from the base medium, further known media contain additions of biological polyamines (J. Biol. Chem., 261, 9502–9508/1986) or bacteropeptones and insulin (Biotechnol. Bioeng., 18, 363–382/1976) or ornithine and/or polyamide (Mol. Cell. Biol., 4, 915–922/1984).

However, these known serum-free media suffer from disadvantages. Thus, during the culturing of the cells, it is frequently necessary to supplement with foetal calf serum. In addition, the transfer of the parent culture, which is usually obtained in a serum-containing medium, into the serum-free medium is only possible by slow adaptation.

Therefore, it is an object of the present invention to provide a serum-free medium which can be used for the growth of non-adherent cells, can be used without problems and is economic. Thus, according to the present invention, there is provided a serum-free culture medium for animal and human cells, especially non-adherent cells, containing a base medium, transferrin, insulin and selenite, wherein it contains or consists of
  2 to 10 mg./liter transferrin,
  2 to 10 mg./liter insulin,
  1 to 10 g./liter peptone,
  10 to 500 mg./liter $\beta$-D-xylopyranose substituted with phosphate, carboxyl and/or sulphate groups,
  0.1 to 0.5 mg./liter selenite and
  0.1 to 2 mg./liter biological polyamine.

The present invention is based upon the surprising discovery that a serum-free culture medium for animal and human cells, which does not display the disadvantages of the previously known media, is obtained when it has a certain content of $\beta$-D-xylopyranose substituted with phosphate, carboxyl and/or sulphate groups. Such $\beta$-D-xylopyranoses are known and commercially available (cf. Merck Index, 10th edition, 1983, Index 7001, P. 1025, Merck and Co., Inc. Rahweh, N.J., U.S.A.) and can be obtained, for example, under the designations pentosan polysulphate, xylan hydrogen sulphate, xylan polysulphate, CB 8061, fibrase, hemoklar, SP 54 (sodium salt) and thrombozite (sodium salt).

Xylopyranoses are ring-shaped sugars originating from xylose.

$\beta$-D-xylopyranoses are preferred with a molecular weight of from 1,00 to 10,000 Dalton and especially preferably with a molecular weight of from 4,000 to 6,000 Dalton. Pentosan polysulphate is quite especially preferred. The concentration of the $\beta$-D-xylopyranose is preferably from 50 to 200 mg./liter and especially preferably from 80 to 120 mg./liter.

As base medium, there can be used all media known for cell culturing, for example DMEM medium, F12 medium and RPMI 1640 medium, which are available, for example, from Boehringer Mannheim GmbH, Mannheim, Germany, and from Gibco BRL Life Technology, Madison, Wis., U.S.A., under these designations. However, it is preferred to use a medium mixture of DMEM/F12 in the ratio of 1:1.

Transferrin is added to the medium in a concentration of from 2 to 10 mg./liter and preferably of from 4 to 6 mg./liter.

The concentration of insulin is from 2 to 10 mg./liter and preferably from 4 to 6 mg./liter.

As peptone, there is preferably used a vegetable peptone, especially preferably from soya bean, in a concentration of from 1 to 10 g./liter and preferably of from 1 to 4 g./liter.

Appropriate biological polyamines include, for example, putrescine, spermidine, spermine and ornithine, putrescine preferably being used. The concentration of the polyamine is from 0.1 to 2 mg./liter and preferably from 0.5 to 1.5 mg./liter.

Selenite is added in a concentration of from 0.1 to 0.5 mg./liter and preferably of from 0.1 to 0.3 mg./liter.

When transfected cells are to be cultured which contain vectors with resistance genes, for the maintenance of the stability of the plasmid transfection, there is additionally added to the medium a selection agent corresponding to the resistance gene contained in the vector. Appropriate selection agents are known to the expert and include, for example, neomycin, hygromycin, mycophenolic acid, hypoxanthine, xanthine, aminopterin and also methotrexate and derivatives thereof.

With the medium according to the present invention, human and animal cells, not only adherent but also suspension cells, can be cultured serum-free. Especially suitable for this purpose are Bowes melanoma cells (Biochem. J., 336, 631–636/1985), human endothelium cells (J. Lab. Clin. Med., 109, 97–104/1987), Sertoli cells (rat) (Biol. Reprod., 34, 895–904/1986), keratocytes (guinea pig) (Dev. Biol. Stand., 60, 439–446/1985), epithelium cells (human, bovine, rabbit) (Exp. Eye Res., 42, 417–431/1986), carcinoma cells (guinea pig) (Cancer Res., 43, 1789/1983), CHO cells (J. Mol. Biol., 159, 601–621/1982) and mouse and human hybridoma cells.

The following Examples are given for the purpose of illustrating but not limiting the present invention. Other embodiments within the spirit and scope of the invention will suggest themselves to those skilled in the art .

EXAMPLE 1 a) Cell culturing

CHO cells (ATCC CCL 61, CHO K1) were cultured in serum-free suspension culture. The culture medium (mixture of DMEM and Ham's F12 medium 1:1) additionally contained 5 mg./liter transferrin, 5 mg./liter insulin, 1 mg./liter putrescine, 0.2 mg./liter selenite, 2 g./liter peptone from soya beans and 100 mg./liter pentosan polysulphate.

$10^5$ cells were seeded out per ml. of medium, placed into roller or spinner flasks and cultured up to the achievement of the maximum cell density ($10^6$ cells/ml. after 120 hours).

b) Determination of the living cell count and of the lactate dehydrogenase activity in cell cultures with and without pentosan polysulphate Culturing was carried out analogously to Example 1 a) and the cell count and the LDH activity determined at various times as a measure for the amount of dead cells which lose LDH. The results obtained are set out in the following Table 1:

TABLE 1

Determination of the living cell count and lactate dehydrogenase (LDH) in cell cultures with and without pentosan polysulphate

| | without pentosan polysulphate | | with pentosan polysulphate | |
|---|---|---|---|---|
| day | cell count $\times 10^5$ | LDH ($\mu$/l.) | cell count $\times 10^5$ | LDH ($\mu$/l.) |
| 0 | 2.5 | 0 | 1 | 0 |
| 1 | 5.7 | 82 | 1.5 | 13 |
| 2 | 4.5 | 120 | 2.2 | 13 |
| 3 | 2.5 | 146 | 4.3 | 15 |
| 4 | 2.8 | 150 | 6.5 | 28 |
| 5 | 3.2 | 228 | 8.7 | 36 |

It can be seen that with pentosan polysulphate there is observed a higher cell count as well as a lesser dying off of the cells (lower LDH activity). Analogous results were obtained with other CHO cell

Example 2

Mouse hybridoma cells (ECACC 84122002, DE 3507849.9) were cultured in serum-free RPMI 1640 medium. The medium additionally contained 5 mg./liter transferrin, 5 mg./liter insulin, 1 mg./liter putrescine, 0.2 mg./liter selenite, 2 g./liter peptone from soya beans and 100 mg./liter pentosan polysulphate.

In the manner described in Example 1, the cells were seeded out and the amount of FSH antibody formed was determined via an ELISA test. The cell growth and the antibody production are shown in the following Table 2:

TABLE 2

| day | cell count $\times 10^5$ | antibody (mg./l.) |
|---|---|---|
| 0 | 1 | 0 |
| 1 | 0.95 | 9.8 |
| 2 | 2.4 | 14.0 |
| 3 | 5.2 | 26.0 |
| 4 | 9.8 | 41.0 |
| 7 | 5.9 | 46.0 |

EXAMPLE 3

LMTK$^-$ cells (ATCC CCL 1.3) were cultured in a serum-free culture, the culture medium used being identical to the medium described in Example 1. $10^5$ cells per ml. of medium were seeded out and cultured up to the achievement of the maximum cell density ($10^6$ cells/ml. after 120 hours).

It was shown that with pentosan polysulphate there was observed not only a higher cell count but also a lesser dying off of the cells (lower LDH activity).

I claim:

1. A method for culturing non-adherent mammalian cells comprising culturing said cells in a medium consisting essentially of
   a base medium,
   2–10 mg/liter of transferrin
   2–10 mg/liter of insulin
   1–10 g/liter of peptone
   10–500 mg/liter beta-D-xylopyranose of a molecular weight range of 1,000–10,000 Dalton. substituted by at least one of a phosphate, carboxyl or sulphate group,
   0.1–0.5 mg/liter selenite, and
   0.1–2 mg/liter biological polyamine.

2. A method for culturing non-adherent mammalian cells selected from the group consisting of Bowes Melanoma, human endothelium, Sertoli, keratocytes, epithelium, carcinoma, hybridoma and CHO cells comprising culturing said cells in the culture medium consisting essentially of
   a base medium of 1:1 DMEM/F12,
   4–6 mg/liter transferrin,
   4–6 mg/liter insulin,
   1–4 g/liter vegetable peptone,
   80–120 mg/liter pentosan sulfate in a molecular weight range of 4,000–6,000 Dalton.,
   0.10–0.30 mg/liter selenite, and
   0.50–1.50 mg/liter putrescine.

3. A serum-free culture medium for non-adherent mammalian cells wherein the medium contains a base medium transferrin, insulin and selenite consisting essentially of a base medium,
   2–10 mg/liter of transferrin,
   2–10 mg/liter of insulin,
   1–10 g/liter peptone,
   10–500 mg/liter beta-D-xylopyranose in a molecular weight range of 1,000–10,000 Dalton wherein said beta-D-xylopyranose is substituted by at least one of a phosphate, carboxyl or sulphate group,
   0.1–0.5 mg/liter selenite, and
   0.1–2 mg/liter biological polyamine.

4. The culture medium of claim 3 wherein the beta-D-xylopyranose has a molecular weight range of 1,000–10,000 Dalton.

5. The culture medium of claim 4 wherein the beta-D-xylopyranose has a molecular weight range of 4,000–6,000 Dalton.

6. The culture medium of claim 3 wherein the concentration range of beta-D-xylopyranose is 50–200 mg/liter.

7. The culture medium of claim 3 wherein the beta—D—Xylopyranose is pentosan polysulfate.

8. The culture medium of claim 3 wherein the base medium is at least one of DMEM, F12 or RPM1 1640 medium.

9. The culture medium of claim 3 wherein the concentration range of transferrin or insulin is 4–6 mg/liter.

10. The culture medium of claim 3 wherein the peptone is vegetable peptone.

11. The culture medium of claim 10 wherein the vegetable peptone is present in a concentration of 1–4 g/liter.

12. The culture medium of claim 3 wherein the biological polyamine is selected from at least one of the group consisting of putrescine, spermidine, spermine and ornithine.

13. The culture medium of claim 3 wherein the biological polyamine is present in a concentration range of 0.5–1.5 mg/liter.

14. The culture medium of claim 3 wherein the selenite is present in a concentration range of 0.1–0.3 mg/liter.

15. The serum-free culture medium of claim 3 for transfected mammalian cells further containing a selection agent corresponding to the resistance gene contained in a vector of the transfected cells.

16. The medium of claim 15 wherein the selection agent is selected from the group consisting of neomycin, hygromycin, mycophenolic acid, hypoxanthine, xanthine, aminopterin, methotrexate and derivatives thereof.

17. A serum-free culture medium for non-adherent mammalian cells wherein the medium contains a base medium, transferrin, insulin and selenite consisting essentially of
a base medium of 1:1 DMEM/F12,
4–6 mg/liter transferrin,
4–6 mg/liter of insulin,
1–4 g/liter vegetable peptone,
80–120 mg/liter pentosan polysulfate in a molecular weight range of 4,999–6,000 Dalton,
0.10–0.30 mg/liter selenite, and
0.5–1.5 mg/liter putrescine.

* * * * *

UNITED STATES PATENT AND TRADEMARK OFFICE
CERTIFICATE OF CORRECTION

PATENT NO. : 5,063,157

DATED : November 5, 1991

INVENTOR(S) : Hubertus Stockinger

It is certified that error appears in the above-identified patent and that said Letters Patent is hereby corrected as shown below:

Col. 2, line 64: change "1789/1983" to -- 1783-1789/1983 --.

Col. 3, line 45: change "cell" to -- cell lines. --.

Col. 6, line 19
Claim 17: change "4,999-6,000 Dalton" to -- 4,000-6,000 Dalton --.

Signed and Sealed this

Tenth Day of August, 1993

Attest:

MICHAEL K. KIRK

*Attesting Officer*  *Acting Commissioner of Patents and Trademarks*